United States Patent [19]

Ballschuh et al.

[11] Patent Number: 5,101,047
[45] Date of Patent: Mar. 31, 1992

[54] SULFOBETAINE-SUBSTITUTED α-SULFONYLCARBOXYLIC ACIDS FROM DIALLYLAMMONIUM SALTS AND A PROCESS FOR THE PREPARATION THEREOF

[76] Inventors: Detlef Ballschuh, Graudenzer Str. 17, BRD, 0-1034 Berlin; Roland Ohme, Waldstr. 6, BRD, 0-1180 Berlin; Horst Seibt, Eugen-Schönhaar-Str. 15, BRD, 0-1055 Berlin; Egon Gründemann, Waldstr. 4, BRD, 0-1180 Berlin, all of Fed. Rep. of Germany

[21] Appl. No.: 629,383

[22] Filed: Dec. 18, 1990

[30] Foreign Application Priority Data

Dec. 21, 1989 [DE] Fed. Rep. of Germany ....... 3360892

[51] Int. Cl.$^5$ .................. C07D 207/08; C07D 207/09; C07D 209/96
[52] U.S. Cl. .................. 548/570; 548/409; 548/568
[58] Field of Search .................. 548/570, 568, 409

[56] References Cited

U.S. PATENT DOCUMENTS 4,410,709 10/1983 Ohme et al. .................. 548/570
4,528,383 7/1985 Schmitt .................. 548/570 X
4,877,885 10/1989 Ballschuh et al. .................. 548/570

Primary Examiner—Joseph Paul Brust

[57] ABSTRACT

The invention relates to novel sulfobetaine-substituted α-sulfonylcarboxylic acids of the general formula I and to processes for the preparation thereof. As organic intermediates, the compounds according to formula I represent a reactive synthesis component having the character of a sulfobetaine and can be used for further syntheses. In the case of a long-chain alkyl radical $R_1$, polyfunctional surfactants are obtained. According to the invention, molar quantities of diallylammonium chloride are reacted with chloroacetic acid and twice the molar quantity of sodium hydrogen sulfite in the presence of a catalytic quantity of a peroxodisulfate, and the reaction solution obtained is converted, after addition of a catalytic quantity of iodide, by heating into sulfobetaine-substituted α-sulfonylacetic acids according to the general formula I.

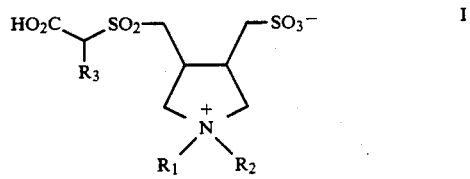

19 Claims, No Drawings

SULFOBETAINE-SUBSTITUTED α-SULFONYLCARBOXYLIC ACIDS FROM DIALLYLAMMONIUM SALTS AND A PROCESS FOR THE PREPARATION THEREOF

The invention relates to novel sulfobetaine-substituted α-sulfonylcarboxylic acids of the general formula I

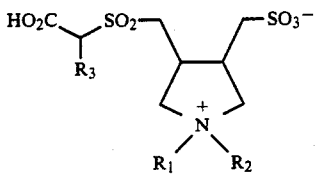

in which

R$_1$ and R$_2$ are hydrogen, a straight-chain or branched alkyl radical having 1 to 22 carbon atoms or an alkyl radical which can contain the group —CH$_2$—CONH— at the start of the chain, or are a -(2'/3'-carboxymethyl-sulfonylmethyl-3'/2'-sulfomethyl)-tetramethylene- radical,
and R$^3$ is hydrogen, a straight-chain or branched alkyl radical having 1 to 22 carbon atoms or an alkyl radical which can contain the group —CH$_2$—CONH— at the start of the chain.

The α-sulfonylcarboxylic acids of the formula I, as organic intermediates of sulfobetaine character, represent a reactive component for further syntheses. If at least one of the substituents R$_1$ to R$_3$ is a long-chain alkyl radical, these compounds can be used as polyfunctional surfactants (anionic sulfobetaine-sulfones).

Sulfobetaine-substituted α-sulfonylcarboxylic acids of the formula I and processes for the preparation thereof have not hitherto been disclosed. Other alkyl- or aryl-α-sulfonylcarboxylic acids have been known for a long time [A. Schöberl and A. Wagner in "Methoden der organischen Chemie [Methods of Organic Chemistry]", Houben-Weyl Volume IX, pages 227 et seq. (1955) or M. Quaedvlieg, ibid. page 298].

According to S. Gabriel, Ber. dtsch. chem. Ges. 14, 833 (1881), for example, the sodium salt of benzenesulfonylacetic acid is first obtained by heating sodium benzenesulfinate with sodium chloroacetate in aqueous solution according to the following equation

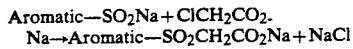

The sulfonylacetic acid can then be set free from the salt by addition of a mineral acid.

This is contradicted by investigations by A. Courtin, H. -R. von Tobel and G. Auerbach, Helv. Chim. Acta 63, 1412 (1980), according to which, on heating of 1 mol of 2-nitrobenzenesulfinic acid, 2 mol of bromoacetic acid and 2 mol of sodium hydroxide solution under reflux conditions for 24 hours, only methyl 2-nitrophenyl sulfone is obtained in 91% yield. Evidently, the carboxymethyl aryl sulfone forming is immediately decarboxylated to the methyl aryl sulfone under the acidic reaction conditions.

Finally, C. S. Marvel and R. S. Johnson, J. org. Chem. 13, 822 (1948) and C. S. Marvel and N. A. Meinhardt, J. Amer. chem. Soc. 73, 859 (1951), apply the "Gabriel synthesis concept" to surfactant-like alkylsulfinates (octanesulfinate to octadecansulfinate) and obtain the sodium salts of the alkanesulfonylacetic acids in yields of between 45 and 85 % by carboxymethylation of molar quantities of sodium alkanesulfinate with sodium chloroacetate.

Very recently, novel sulfobetaine-substituted sulfinic acids and salts thereof have become available as potential starting materials for the synthesis of novel sulfobetaine-substituted α-sulfonylcarboxylic acids as industrially easily accessible compounds.

Such sulfobetaine-sulfinates are obtained by free radical-initiated sulfocyclosulfination of diallylammonium salts with hydrogen-sulfite according to DD 225,128 A1 or EP 163,319 A3.

However, attempts carried out in accordance with the state of the art, for example, to carboxymethylate sodium 1,1-dimethyl-3-sulfinatomethyl-4-sulfomethyl-pyrrolidinium betaine (sulfobetaine-sulfinate) with sodium chloroacetate to give the corresponding sulfobetaine-substituted α-sulfonylacetic acid, failed. The reaction solution obtained, which was composed of a complex mixture of starting products, secondary products and also the target product, did not allow work up to give the desired sulfonylacetic acid because of the polar character of the starting products and reaction products.

Thus, no process for converting sulfobetaine-sulfinates to pure sulfobetaine-substituted α-sulfonylcarboxylic acids is in existence.

Moreover, neither has a two-stage synthesis process been disclosed which makes sulfobetaine-substituted α-sulfonylcarboxylic acids accessible directly from the sulfobetaine-substituted sulfinates produced in situ from diallylammonium salts and hydrogen sulfites in the presence of α-halogenocarboxylic acids.

The subject of the invention is a simple two-stage synthesis process for the preparation of sulfobetaine-substituted α-sulfonylcarboxylic acids from easily accessible and industrially available starting materials, such as a diallylammonium salt, hydrogen sulfite and α-halogenocarboxylic acids, which allows the process steps to be carried out without the formation of by-products with, at the same time, a high purity and yield of the target product.

The preparation of the compounds of the formula I is carried out by reacting, in a first process step, diallylammonium salts, preferably diallylammonium chlorides of the general formula II

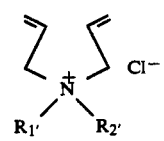

in which

R$_1$ and R$_2$ are hydrogen, a straight-chain or branched alkyl radical having 1 to 22 carbon atoms or an alkyl radical which can contain the group —CH$_2$—CONH— at the start of the chain, or are allyl radicals, with molar quantities of an α-halogenocarboxylic acid, preferably an α-chlorocarboxylic acid of the general formula III

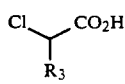

in which

R₃ is as defined above,
and twice the molar quantity of a metal hydrogen sulfite, preferably sodium hydrogen sulfite, with one another in the presence of a catalytic quantity of a peroxodisulfate and, in the subsequent second process step, heating the reaction solution obtained, after addition of a catalytic quantity of an iodide soluble in the reaction medium, to the boil until the sulfinate content of the reacting solution has fallen to virtually zero.

The overall reaction, i.e. the free radical-initiated sulfocyclosulfination of the diallylammonium salt with a coupled carboxyalkylation of the sulfobetaine-sulfinate formed in situ, in two process steps is illustrated by the following equations:

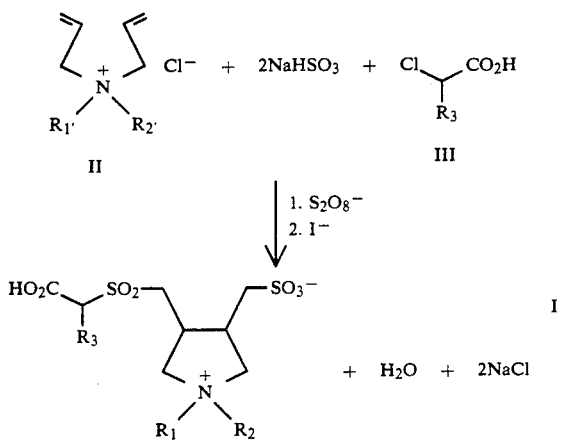

The sulfocyclosulfination of a diallyl- or tetraallylammonium salt proceeds, according to DD 225,128 A1, with the maximum yield of sulfocyclosulfination product (sulfobetaine-sulfinate) only if pH conditions of around 2 are maintained. The adjustment to this pH is achieved by addition of a mineral acid to the mixture of the diallylammonium salt and hydrogensulfite. Corresponding pH adjustments using an α-halogenocarboxylic acid have not hitherto been carried out. It can therefore be regarded as a surprising finding that, for example, the addition of 1 mol of chloroacetic acid to a mixture of 1 mol of diallylammonium salt and 2 mol of technical sodium hydrogen sulfite solution gives the optimum starting pH of around 2, i.e. conditions which correspond to the goal stated above. The order of the combination of the reactants is of no importance to the course of the reaction.

Depending on the quality of the sodium hydrogen sulfite solution used, slight pH fluctuations can occur. They can be corrected either by adding a small quantity of a mineral acid or by starting the reaction with a part quantity of the halogenocarboxylic acid and adding the residual quantity of the halogenocarboxylic acid only after the first reaction stage.

When, for example, tertiary diallylamines are used as the starting products of the reaction, these should preferably be dissolved in the halogenocarboxylic acid and the starting pH should be adjusted with a mineral acid after the addition of the hydrogen sulfite solution.

Since, in the case of tertiary diallylamines and a starting pH of 2.5, the sulfocyclosulfination already proceeds to completion, less than the equivalent molar quantity of mineral acid is required for the formation of the diallylammonium salt.

For carrying out the first process step, 1 to 5 mol % of peroxodisulfate, relative to the diallylammonium salt employed, is added to the starting solution, which has been prepared in this way and which should have a temperature between 20° and 30° C., in order to initiate the sulfocyclosulfination reaction.

It has here proved to be preferable to add the peroxodisulfate in two portions, in order to achieve the most complete conversion possible, quantities of 2 times 2 mol % relative to the diallylammonium salt employed, being fully sufficient in most cases. Sodium, potassium or ammonium peroxodisulfate, which can be employed either as a solution or in powder form, are suitable as the peroxodisulfates. After the addition of peroxodisulfate, the initially pale yellow starting solution assumes a red to blood-red color, but it brightens considerably, shortly after the temperature maximum has been passed.

To initiate the second process step, a catalytic quantity of a soluble iodide, for example sodium iodide, potassium iodide, or ammonium iodide, and if appropriate the particular α-iodocarboxylic acid, for example iodoacetic acid, is added to the reacting solution and this solution is further heated with evaporative cooling until sulfinate is no longer detectable in the reacting solution by bromatometric titration.

When a quantity of 5 to 50 mmol of sodium, potassium or ammonium iodide/mol of diallylammonium salt is employed, complete conversions are reached in the course of one to two hours. Whereas quantities of less than 3 mmol of the abovementioned iodides no longer show any catalytic action, quantities larger than 7 mmol further accelerate the reaction, but later discolor the crystalline target . products.

If the carboxyalkylation of the sulfocyclosulfination product is carried out without iodide addition, the desired conversion admittedly takes place in the initial phase, but it slows down with increasing reaction time to such an extent that there is no lack of secondary reactions and, as a result, the desired reaction product cannot be isolated, because the latter is also decomposed under continuous thermal stress.

A further surprising fact in this second process step is that the sulfocyclosulfination product of the diallylammonium salt can be carboxyalkylated at a low pH at the boil, even though it is known [W. Jeblick and W. Bunge in "Ullmanns Encyklopädie der technischen Chemie [Ullmann's Encyclopaedia of Industrial Chemistry]", Volume 22 (1982), page 315] that sulfinic acids preferentially disproportionate to a thiosulfonic acid S-ester and sulfonic acids under such conditions-low pH and high temperatures.

On the other hand, it was regarded as necessary, according to the state of the art, to obtain α-sulfonylcarboxylic acids by reacting the metal salts of sulfinic acids or α-halogenocarboxylic acids, when it was not possible to exclude side reactions, such as a decarboxylation of the target product, in all cases.

By contrast, it is possible, in a special embodiment of the process, also to carry out the second synthesis step separately. For this purpose, either a mole equivalent of a base can be added to molar quantities of isolated sulfobetaine-sulfinic acid and α-halogenocarboxylic acid or the metal salt of one acid can be reacted with the particular other acid.

The reaction products thus obtained are identical to those which are produced by the two-stage synthesis process. This approach does not have any process advantage in principle, since the starting sulfobetaine-sulfinates required for this purpose must be prepared beforehand from the diallylammonium salts.

As compared with the procedure of the state of the art, however, the free α-sulfonylcarboxylic acids are obtained directly in an advantageous manner, whereby first the neutralization and, after reaction has taken place, the liberation of the carboxylic acid functional group are avoided.

Furthermore, side reactions are prevented in the procedure, so that it must be regarded as substantially more economical.

In summary, the advantage of the invention is represented by a simple synthesis which makes the hitherto unknown sulfobetaine-substituted α-sulfonylcarboxylic acids of the general formula I directly accessible from diallylammonium salts without the isolation of intermediates. The starting materials utilized are intermediates which are available on an industrial scale and which can be caused to react in short reaction times by simple means. The invention will be explained in more detail by the examples which follow.

EXAMPLES

EXAMPLE 1

1,1-Dimethyl-3-carboxymethylsulfonylmethyl-4-sulfomethyl-pyrrolidinium betaine ($R_1=R_2=CH_3$; $R_3=H$ in the general formula I)

a) 307.4 g (1 mol) of 52.6 % aqueous dimethyldiallylammonium chloride solution, 118.1 g (1 mol) of 80% aqueous chloroacetic acid and 539 g (2.02 mol) of 39% technical sodium hydrogen sulfite solution are introduced into a 1.5 l sulfination flask, which is fitted with a stirrer, thermometer, reflux condenser and a heat source, and mixed with one another with stirring. This gives a pale yellow, homogeneous solution at 21° C. and a starting pH of 2.02. To initiate the reaction, 2 mol % (4.56 g) of ammonium peroxodisulfate are first added and a minute later—the reaction temperature has risen to 60° C. in the meantime and the reaction solution has assumed a blood-red color—a further 2 mol % of ammoniumperoxodisulfate are added. The reaction temperature maximum of 76° C. is already reached after one further minute. 1.05 g (7 mmol) of sodium iodide are added to the reaction solution, and this is heated for 90 minutes to the boil at 110° C. The red reaction solution decolorises already during the heating-up and is pale yellow when the boiling point is reached. The red coloration of the solution is caused by iron(III) 1,1-dimethyl-3-sulfinatomethyl-4-sulfomethyl-pyrrolidinium betaine, which is formed from the reaction intermediate 1,1-dimethyl-3-sulfinatomethyl-4-sulfomethyl-pyrrolidinium betaine and the traces of iron salts present in the technical hydrogen sulfite solution used. At this point in time, the reaction is already quantitatively complete, i.e. the reaction intermediate 1,1-dimethyl-3-sulfinatomethyl-4-sulfomethyl-pyrrolidinium betaine is no longer detectable by bromatometric titration of a sample of the reaction solution. (If, however, the reaction is carried out without addition of iodide, the conversion is 86% after 90 minutes and 94% after 360 minutes and, in parallel thereto, considerable decarboxylation of the target product takes place.) To increase the later yield of crystalline target product, water can be distilled off from the reaction solution for concentrating already during the boiling phase. For complete crystallization, the mixture is allowed to cool and to stand overnight. For working up, the crystal mass is sharply filtered off with suction from the mother liquor, the crystals are washed with a little water and twice with alcohol and, after drying in air, 250 g of a white, loose crystal powder are obtained which can still be recrystallized from water for fine purification. This gives very pure 1,1-dimethyl-3-carboxymethylsulfonylmethyl-4-sulfomethyl-pyrrolidinium betaine dihydrate (melting point: starting at 290° C. with decomposition).

—C-NMR spectrum of the sodium salt ($H_2O$; external standard tetramethylsilane-TMS; $\delta=0.0$ ppm):

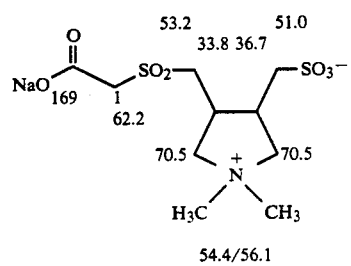

The numerical data on the atom symbols correspond to the chemical shifts for the cis-configuration (3,4-position) in ppm. The N—CH$_3$ groups are not equivalent and, as with the N—CH$_2$ groups, there is an additional signal splitting due to the $^{14}N$ quadrupole moment. By contrast, a $^{13}C$-NMR spectrum taken in $D_2O$ shows that the methylene group between the carboxylate group and the sulfone group has a pronounced acidic CH character, which is detectable by a sharp decrease in the intensity of the signal at 62.2 ppm due to H/D exchange.

b) 30.7 g (0.1 mol) of 1,1-dimethyl-3-sulfinatomethyl-4-sulfomethyl-pyrrolidinium betaine dihydrate (prepared from dimethyldiallylammonium chloride and sodium hydrogen sulfite; cf. DD 225,128 A1, Example 13), 12.1 g (0.1 mol) of 33% sodium hydroxide solution, 11.8 g (0.1 mol) of 80% aqueous chloroacetic acid, 0.15 g (1 mmol) of sodium iodide and 20 g of water are mixed with one another and heated to the boil for 30 minutes. Already after a short reaction time, crystals of the target product precipitate from the initially clear, colorless solution. After cooling of the reaction solution, the target product can be isolated as the dihydrate in more than 90% yield. The $^{13}C$-NMR spectrum of the sodium salt of the crystalline product obtained is fully identical to that prepared according to Example 1a.

EXAMPLE 2

1,1-Dimethyl-3-(1'-carboxyethylsulfonylmethyl)-4-sulfomethyl-pyrrolidinium betaine ($R_1=R_2=R_3=CH_3$ in the general formula I)

The procedure followed is as in Example 1a, in a mixture of 61.5 g (0.2 mol) of 52.6% aqueous dimethyldiallylammonium chloride solution, 107.8 g (0.404 mol) of 39% technical sodium hydrogen sulfite solution and 21.7 g (0.2 mol) of 2-chloropropionic acid - the 2-chloropropionic acid is not completely dissolved at the mixing temperature of the reactants of 28° C.; a pH of 2.3 establishes itself in the mixture-is reacted with two portions of 0.91 g each (2 mol %) of ammonium peroxodisulfate. After the reaction temperature maximum of 79° C. has been reached within 90 seconds, 0.2 g (1.3 mmol) of sodium iodide is added to the solution which is now a lemon yellow color, and the mixture is heated at the boil for 2 hours. The cooled reaction solution is stored for some time in a refrigerator, and the target product is isolated in about 60% yield as well-formed colorless crystals. For fine purification, it can still be recrystallized from water (melting point: 215° to 218° C.). A second crystalline fraction of the target product can also be obtained by working up the mother liquor. Because of the low solubility of the free carboxylic acid in water at room temperature, a sample is converted into the more readily soluble calcium salt by reaction with calcium carbonate (melting point: starting at 270° C. with decomposition).

$^{13}$C-NMR spectrum of the calcium salt (D$_2$O; external standard TMS; $\delta = 0.0$ ppm):

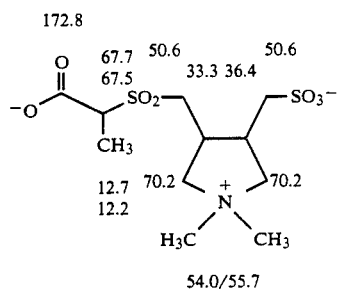

The N—CH$_3$ groups are not equivalent and, as in the case of the CH$_2$ groups, there is also additional signal splitting due to the $^{14}$N quadrupole moment. The signal doublings at 67.5/67.7 ppm and 12.2/12.7 ppm are to be ascribed to the various asymmetry centers in the molecule.

EXAMPLE 3

1,1-Dimethyl-3-(1'-carboxypropylsulfonylmethyl)-4-sulfomethyl-pyrrolidinium betaine ($R_1=R_2=CH_3$; $R_3=C_2H_5$ in the general formula I)

The procedure followed is as in Examples 1 and 2, and the target product is obtained in more than 90% yield in the form of colorless crystals (melting point: 198°-200° C.; melting point of the calcium salt: 225°-227° C.).

$^{13}$C-NMR spectrum of the calcium salt (D$_2$O; external standard TMS; $\delta = 0.0$ ppm):

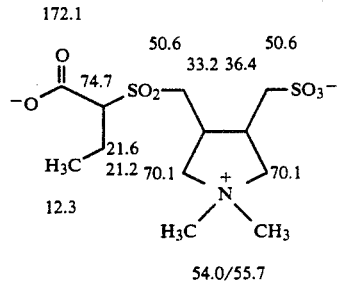

The N—CH$_3$ groups are not equivalent and, as in the case of the N—CH$_2$ groups, there is also additional signal splitting due to the $^{14}$N quadrupole moment. The signal doubling at 21.2/21.6 ppm is to be ascribed to the various asymmetry centers in the molecule.

EXAMPLE 4

1,1-Dimethyl-3-(1'-carboxypentylsulfonylmethyl)-4-sulfomethyl-pyrrolidinium betaine ($R_1=R_2=CH_3$; $R_3=C_4H_9$ in the general formula I)

The procedure followed is as in Example 1b, and a mixture of 15.35 g (50 mmol) of 1,1-Dimethyl-3-sulfinic acid methyl-4-sulfomethyl-pyrrolidinium betaine, 9.75 g (50 mmol) of 2-bromohexanoic acid, 2.5 g (25 mmol) of calcium carbonate, 0.3 g (2 mmol) of sodium iodide and 10 g of water is reacted with heating-initially with evolution of carbon dioxide-until the sulfinate content of the solution has fallen to virtually zero. A further 2.5 g (25 mmol) of calcium carbonate are then added and the calcium salt forming is left to crystallize. Rinsing with alcohol gives a colorless calcium salt, freed of sodium iodide, of the target product in more than 90% yield, which can be recrystallized from water for fine purification.

Melting point: starting at 260° C. with decomposition. $^{13}$C-NMR spectrum of the calcium salt (D$_2$O; external standard TMS; $\delta = 0.0$ ppm):

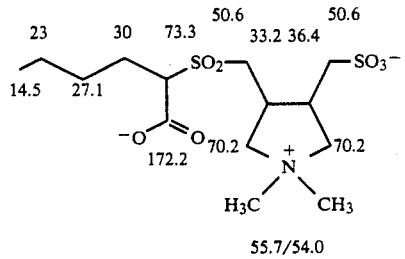

The N—CH$_3$ groups are not equivalent (cis-compound-relative to the substituents in the 3- and 4-positions) and, as in the case of the N—CH$_2$ groups, there is an additional signal splitting due to the $^{14}$N quadrupole moment.

EXAMPLE 5

Sodium 1,1-(2'/3'-carboxymethylsulfonylmethyl-3'/2'-sulfomethyl)-tetramethylene-3-carboxymethylsulfonyl-methyl-4-sulfomethyl-pyrrolidinium betaine isomer mixture from tetraallylammoniumbromide

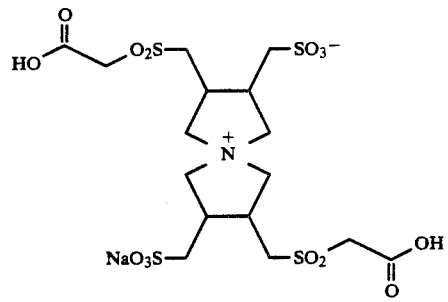

The procedure followed is as in Example 1a, and a mixture of 25.8 g (0.1 mol) of tetraallylammonium bromide dissolved in 25 g of water, 107.8 g (0.404 mol) of 39% technical sodium hydrogen sulfite solution and 23.6 g (0.2 mol) of 80% chloroacetic acid-pH of the mixture 2.2—is reacted with two portions each of 0.46 g (2 mol %) of ammonium peroxodisulfate. The reaction temperature thus rises from 25° to 64° C. After addition of 0.15 g (1 mmol) of sodium iodide and heating to the boil for two hours, the intermediate is no longer detectable by bromatometry. The reaction solution is concentrated, the residue is treated with methanol and, after drying in air, a colorless crystalline substance is obtained (melting point: 210° C.).

EXAMPLE 6

1-Dodecyl-3-carboxymethylsulfonylmethyl)-4-sulfomethyl-pyrrolidinium betaine ($R_1=R_3=H$; $R_2=C_{12}H_{25}$ in the general formula I)

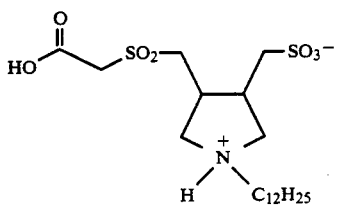

The procedure followed is as in Example 1a, and a mixture at pH 2 of 26.55 g (0.1 mol) of diallyldodecylamine, 11.8 g (0.1 mol) of 80% aqueous chloroacetic acid, 53.9 g (0.202 mol) of 39% technical sodium hydrogen sulfite solution and 7 g of 37% hydrochloric acid is reacted with 2 portions each of 0.46 (2 mol %) of ammoniumperoxodisulfate. The reaction temperature thus rises from 24° to 62° C. This gives a viscous, clear yellow solution which, after the addition of 0.15 g (1 mmol) of sodium iodide and heating for two hours at 106° C., has been quantitatively converted to the target product. After cooling, the reaction solution separates into two phases, the upper phase containing the target product as a viscous solution.

EXAMPLE 7

1-Dodecyl-1-methyl-3-carboxymethylsulfonylmethyl-4-sulfomethyl-pyrrolidinium betaine ($R_1=CH_3$; $R_2=C_{12}H_{25}$; $R_3=H$ in the general formula I)

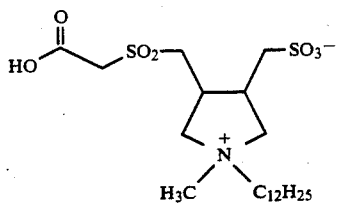

The procedure followed is as in Examples 1a and 6, and a mixture at pH 2 of 36.04 g (0.1 mol) of 80% dodecylmethyldiallylammonium bromide, 11.8 g (0.1 mol) of 80% chloroacetic acid and 53.9 g (0.202 mol) of 39% sodium hydrogen sulfite solution is reacted with two portions each of 0.46 g (2 mol %) of ammoniumperoxodisulfate. 0.15 g (1 mmol) of sodium iodide is then added and the mixture is heated to the boil for 2 hours under reflux conditions. This gives an amber-colored, homogeneous solution of the target product. A white crystal powder which starts to decompose at 156° C. can be isolated in more than 90% yield from this solution by extraction with n-butanol, followed by removal of the n-butanol by distillation, dissolution of residue with gentle heating in ethanol and allowing to crystallize. The pulverulent α-sulfonylacetic acid has a fairly low solubility in water (20° C.), but is easily soluble, with vigorous foaming, by shaking with dilute sodium hydroxide solution.

We claim:

1. A sulfobetaine-substituted α-sulfonylcarboxylic acid from a diallylammonium salt, of the formula I

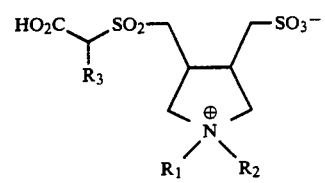

in which $R_1$ and $R_2$ are hydrogen, a straight-chain or branched alkyl radical having 1 to 22 carbon atoms or a radical —$CH_2CONH$-alkyl, or are either a -(2'-carboxylemthyl-sufonylmethyl-3'-sulfomethyl)-tetramethylene-radical, or -(3'-carboxymethyl-sulfonylmethyl-2'-sulfomethyl)-tetramethylene- or mixture thereof, $R_3$ is hydrogen, a straight-chain or branched alkyl radical having 1 to 22 carbon atoms or a radical —$CH_2CONH$-alkyl.

2. A compound as claimed in claim 1, wherein $R_1$ and $R_2$ are —$CH_3$ and $R_3$ is hydrogen.

3. A compound as claimed in claim 1, wherein $R_1$, $R_2$ and $R_3$ are —$CH_3$.

4. A compound as claimed in claim 1, wherein $R_1$, and $R_2$ are —$CH_3$ and $R_3$ is —$C_2H_5$.

5. A compound as claimed in claim 1, wherein $R_1$ and $R_2$ are —$CH_3$ and $R_3$ is —$C_4H_9$.

6. A compound as claimed in claim 1, wherein $R_1$ and $R_3$ are hydrogen and $R_2$ is —$C_{12}H_{25}$.

7. A compound as claimed in claim 1, wherein $R_1$ is —$CH_3$, $R_2$ is —$C_{12}H_{25}$ and $R_3$ is hydrogen.

8. A compound as claimed in claim 1, wherein $R_1$ is —$CH_3$ or H.

9. A process for the preparation of a sulfobetaine substituted α-sulfonylcarboxylic acid of the formula I as claimed in claim 1, which comprises reacting, in a first process step, a diallylammonium salt, in a solution with a molar quantity of an α-monohalogenacetic acid and twice the molar quantity of a hydrogen sulfite, with one another to sulfobetaine sulfinate in the presence of a catalytic quantity of a peroxodisulfate and, in the second process step, heating the reaction solution obtained, after addition of a catalytic quantity of iodide, to the boil until the sulfinate content of the reacting solution has fallen to zero.

10. The process as claimed in claim 9, wherein the diallylammonium salt is a diallylammonium chloride of the formula II

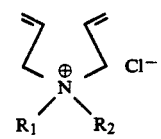

in which
$R_1$ and $R_2$ are hydrogen, a straight-chain or branched alkyl radical having 1 to 22 carbon atoms a radical —$CH_2CONH$— alkyl, or are allyl radicals.

11. The process as claimed in claim 9, wherein the α-monohalogencarboxylic acid is an α-chlorocarboxylic acid of the formula

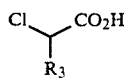    III in which $R_3$ is hydrogen, a straight-chain or branched alkyl radical having 1 to 22 carbon atoms or a radical —$CH_2CONH$-alkyl.

12. The process as claimed in claim 9, wherein the peroxodisulfate is added in two portions of each of 2 mol %, relative to the diallylammonium salt employed.

13. The process as claimed in claim 9, wherein 1 to 5 mol % of peroxodisulfate, relative to the diallylammonium salt employed, are added as the catalyst in the first process step.

14. The process as claimed in claim 13, wherein the peroxodisulfate is added in two portions each of 2 mol %, relative to the diallylammonium salt employed.

15. The process as claimed in claim 9, wherein 5 to 50 mol of sodium iodide, potassium iodide or ammonium iodide/mol of diallylammonium salt are added as the catalyst in the second process step.

16. The process as claimed in claim 9, wherein said peroxodisulfate is ammonium peroxodisulfate.

17. The process as claimed in claim 9, wherein said peroxodisulfate is sodium peroxodisulfate.

18. The process as claimed in claim 9, wherein said peroxodisulfate is potassium peroxodisulfate.

19. The process as claimed in claim 9, wherein said hydrogen sulfite is sodium hydrogen sulfite.

* * * * *

UNITED STATES PATENT AND TRADEMARK OFFICE
CERTIFICATE OF CORRECTION

PATENT NO. : 5,101,047
DATED : March 31, 1992
INVENTOR(S) : Detlef Ballschuh, et al.

It is certified that error appears in the above-identified patent and that said Letters Patent is hereby corrected as shown below:

In col. 4, at line 3 delete ".".

In col. 4, at line 39 delete ".".

In col. 6, at line 15 "-C-NMR" should read --$^{13}$C-NMR--.

In claim 1, col. 10, at lines 20-21 "-(2'-carboxylemthyl-" should read
-- -(2'-carboxylmethyl- --.

In claim 9, col. 10 at line 46 "α-monohalogenacetic" should read
--α-monohalogencarboxylic--.

Signed and Sealed this

Ninth Day of November, 1993

Attest:

BRUCE LEHMAN

*Attesting Officer*       *Commissioner of Patents and Trademarks*